United States Patent [19]

Takaku et al.

[11] Patent Number: 5,474,928
[45] Date of Patent: Dec. 12, 1995

[54] **ARGININE DEIMINASE FROM A *MYCOPLASMA ARGININI* STRAIN**

[75] Inventors: Karuo Takaku, Saitama; Kaoru Miyazaki, Kanagawa; Miho Aoshima, Saitama, all of Japan

[73] Assignee: Nippon Mining Company, Limited, Tokyo, Japan

[21] Appl. No.: 201,724

[22] Filed: Feb. 25, 1994

Related U.S. Application Data

[63] Continuation of Ser. No. 37,713, Mar. 24, 1993, abandoned, which is a continuation of Ser. No. 558,158, Jul. 26, 1990, abandoned.

[30] Foreign Application Priority Data

Aug. 2, 1989 [JP] Japan .................................. 1-200902

[51] Int. Cl.⁶ .............................. C12N 9/80; C12N 9/78
[52] U.S. Cl. ............................. 435/228; 435/227
[58] Field of Search ........................ 435/227, 228

[56] References Cited

PUBLICATIONS

Sasaki et al., *In Vitro*, vol. 20, No. 5, May 1984, pp. 369–375.
Chen et al., *J. Clin. Microb.*, vol. 16, No. 5, Nov. 1982, pp. 909–919.
Lin, J., *J. Gen. Microb.*, vol. 132, 1986, pp. 1467–1474.
Fujsaki et al., *J. Biochem.*, vol. 89, No. 1, 1981, pp. 257–263.
Takahara et al., *J. Biochem*, vol. 94, No. 6, 1983, pp. 1945–1953.
Baur et al., *Eur. J. Biochem*, vol. 179, No. 1, Jan. 1989, pp. 53–60.
Journal Of Chromatography, vol. 440, 1988, pp. 131–140 Elsevier Science Publishers B. V., Sugimura, et al.

*Primary Examiner*—Charles L. Patterson, Jr.
*Assistant Examiner*—Keith D. Hendricks
*Attorney, Agent, or Firm*—Burgess, Ryan & Wayne

[57] ABSTRACT

A novel arginine deiminase of an approximately 45,000 molecular weight derived from mycoplasma having an ability to decompose arginine, and the method of manufacturing this novel enzyme from mycoplasma. This enzyme is an effective anti-cancer agent, as it shows anti-cancer activities both in vitro and in vivo.

2 Claims, 7 Drawing Sheets

FIG. 4A

```
TCT GTA TTT GAC AGT AAA TTT AAA GGA ATT CAC GTT TAT TCA GAA ATT      48
Ser Val Phe Asp Ser Lys Phe Lys Gly Ile His Val Tyr Ser Glu Ile
 1           5               10              15

GGT GAA TTA GAA CCA GTT CTA CAC GTT CAC GAA CCA GGA CGC GAA ATT GAC   96
Gly Glu Leu Glu Pro Val Leu His Val His Glu Pro Gly Arg Glu Ile Asp
         20              25              30

TAT ATT ACA CCA GCT AGA CTA GAT GCT AGA AAA CTA TTC TCA GCT ATC TTA  144
Tyr Ile Thr Pro Ala Arg Leu Asp Ala Arg Lys Leu Phe Ser Ala Ile Leu
         35              40              45

GAA AGC CAC GAT CAC AAA AGA AAA GAA CAC GTT GTT CAA GAA ATC TTA GAA  192
Glu Ser His Asp His Lys Arg Lys Glu His Val Val Gln Glu Ile Leu Glu
     50              55              60

AAA GCA AAC GAT ATC AAT GTT AAT GCA GAA TCA CAA GTT CTA GCT TTA      240
Lys Ala Asn Asp Ile Asn Val Asn Ala Glu Ser Gln Val Leu Ala Leu
 65              70              75              80

ACA TAT GAT TTA GAT AAA AAA GCT GAA GAA AAA CAC CCA GTA AAA GCA GAA  288
Thr Tyr Asp Leu Asp Lys Lys Ala Glu Glu Lys His Pro Val Lys Ala Glu
         85              90              95

TTT TTA GAA GAC AAA AAA TCA GAA GAA CAC AAA GAA GAA GAA GTT GTT GAA  336
Phe Leu Glu Asp Lys Lys Ser Glu Glu His Lys Glu Glu Glu Val Val Glu
     100             105             110

GTA AGA AAC TTC TTA AAA TAC GAT TTA AGA GAA CAC AAA GAA GTA GTA GAA  384
Val Arg Asn Phe Leu Lys Tyr Asp Leu Arg Glu His Lys Glu Val Val Glu
         115             120             125

ATC ATG ATG GCA GGG ATC ACA ATC TAC GAT TTA GGT ATC GAA GCA GAT      432
Ile Met Met Ala Gly Ile Thr Ile Tyr Asp Leu Gly Ile Glu Ala Asp
         130             135             140
```

FIG. 4B

```
CAC GAA TTA ATC GTT GAC CCA ATG CCA AAC CTA TAC TTC ACA CGT GAC  480
His Glu Leu Ile Val Asp Pro Met Pro Asn Leu Tyr Phe Thr Arg Asp
145                 150                 155                 160

CCA TTT GCA TCA GTA GGT AAT GGT GTA ACA CAC TAC ATC TAC ATG TAC  528
Pro Phe Ala Ser Val Gly Asn Gly Val Thr His Tyr Ile Tyr Met Tyr
         165                 170                 175

AAA AGA CAA CGT GAA CAA ACA TTA TTC TCA AGA TTT GTA CCA TTC AAT  576
Lys Arg Gln Arg Glu Gln Thr Leu Phe Ser Arg Phe Val Pro Phe Asn
180                 185                 190

CAC CCT AAA CTA ATT AAC ACT ACT CCA GTA TGA TAC TAC TAC GAC AAA  624
His Pro Lys Leu Ile Asn Thr Thr Pro Val Trp Tyr Tyr Tyr Asp Lys
         195                 200                 205

TTA TCA ATC GAA GGT GGG GAC GTA GAC GTA TTT ATC TAC AAC AAT AAT  672
Leu Ser Ile Glu Gly Gly Asp Val Asp Val Phe Ile Tyr Asn Asn Asn
210                 215                 220

GTA GTT GGT GTT TCT GAA AGA ACT GAC TTA CAA ACA GTT GTA CTA TTA  720
Val Val Gly Val Ser Glu Arg Thr Asp Leu Gln Thr Val Val Leu Leu
225                 230                 235                 240

GCT AAA AAC ATT GTT CCA AAT GCT AAA GAA TTC GAA TGT ACA ACT ACT  768
Ala Lys Asn Ile Val Pro Asn Ala Lys Glu Phe Glu Cys Thr Thr Ile
         245                 250                 255

GCA ATT AAC GTT CCA CCA AAA TGA ACA AAC AAC ATG CAC TTA GAC CGT  816
Ala Ile Asn Val Pro Pro Lys Trp Thr Asn Asn Met His Leu Asp Arg
260                 265                 270

CTA ACA ATG TTA GAC AAG GAC TTT CTA TAC TCA CCA TCA GAC ACA GCT  864
Leu Thr Met Leu Asp Lys Asp Phe Leu Tyr Ser Pro Ser Asp Thr Ala
         275                 280                 285

GAC GTA TTT AAA TTC TGA GAT TAT GAC TTA GTA AAC GGT GGA GCA AAT  912
Asp Val Phe Lys Phe Trp Asp Tyr Asp Leu Val Asn Gly Gly Ala Asn
290                 295                 300
```

```
CCA CAA CCA GTT GAA AAC GGA TTA CCT CTA GAA GGA TTA TTA CAA TCA          960
Pro Gln Pro Val Glu Asn Gly Leu Pro Leu Glu Gly Leu Leu Gln Ser
305                 310                 315                 320

ATC ATT AAC AAA AAA CCA GTT TTA ATT CCT ATC GCA GGT GAA GGT GCT         1008
Ile Ile Asn Lys Lys Pro Val Leu Ile Pro Ile Ala Gly Glu Gly Ala
            325                 330                 335

TCA CAA ATG GAA ATC GAA AGA GAA ACA CAC TTC GAT GGT ACA AAC TAC         1056
Ser Gln Met Glu Ile Glu Arg Glu Thr His Phe Asp Gly Thr Asn Tyr
                340                 345                 350

TTA GCA ATT AGA CCA GGT GTT GTA ATT GGT TAC TCA CGT AGA AAA             1104
Leu Ala Ile Arg Pro Gly Val Val Ile Gly Tyr Ser Arg Asn
                    355                 360                 365

ACA AAC GCT GCT CTA GAA GCT GCA CGC ATT AAA GTT CTT CCA TTC CAC         1152
Thr Asn Ala Ala Leu Glu Ala Ala Arg Ile Lys Val Leu Pro Phe His
        370                 375                 380

GGT AAC CAA TTA TCA TTA GGT ATG GGT AAC GCT CGT TGT ATG TCA ATG         1200
Gly Asn Gln Leu Ser Leu Gly Met Gly Asn Ala Arg Cys Met Ser Met
385                 390                 395                 400

CCT TTA TCA CGT AAA GAT GTT AAG TGA                                     1227
Pro Leu Ser Arg Lys Asp Val Lys Trp
            405

FIG. 4C
```

```
AAA TTT AAA GGT ATT CAT GTT TAT
Lys Phe Lys Gly Ile His Val Tyr
```
FIG. 5

```
AAA TTT AAA GGA ATT CAT GTT TAT
Lys Phe Lys Gly Ile His Val Tyr
```
FIG. 6

```
AAA TTT AAA GGA ATT CAT GTA TAT
Lys Phe Lys Gly Ile His Val Tyr
```
FIG. 7

```
AAA TTT AAA GGT ATT CAT GTA TAT
Lys Phe Lys Gly Ile His Val Tyr
```
FIG. 8

ARGININE DEIMINASE FROM A *MYCOPLASMA ARGININI* STRAIN

This application is a continuation, of application Ser. No. 08/037,713, filed Mar. 24, 1993, now abandoned which is a continuation, of application Ser. No. 07/558,158, filed Jul. 26, 1990, now abandoned.

BACKGROUND OF THE INVENTION

The present invention relates to a novel arginine deiminase and the manufacturing method thereof. Further, the present invention relates to an anti-cancer agent containing this arginine deiminase as an effective ingredient.

DESCRIPTION OF THE RELATED ART

Recently, increasing attention is focused on the fresh attempt to cure cancer by using enzymes on the basis of the requirement of nourishment by cancer cells. In other words, this treatment attempts to inhibit the growth of, or necrotize, the cancer cells by decomposing the nourishment required by the cancer cells and thus by shutting out the source of nourishment from the reach of the cancer cells. Among these anti-tumor enzymes, L-asparaginase (EC 3.5.1.1) [see Nature, 229, 168(1971)] and arginase (EC 3.5.3.1) [Br. J. Cancer, 19, 379(1965)] are known. However, L-asparaginase is effective only to a few types of cancer such as leukemia and malignant lymphoma because there are a small number of cancers dependent on L-asparagine, while arginase fails to show anti-cancer activities in vivo although it shows inhibiting activities against the growth of a variety of cancer cells in vitro [Br. J. Cancer, 30, 50(1974)].

Moreover, although there have been reports that arginine deiminase is obtainable from mycoplasma and other microorganisms [J. Biol. Chem., 241, 2228–2236 (1966),ibid., 252, 2615–2620 (1987), ibid., 250, 4580–4583 (1975), Arch. Biochem. Biophys. 69, 186–197 (1957), etc.], no reports have mentioned the anti-cancer activity of this enzyme.

SUMMARY OF THE INVENTION

It is an object of the present invention to provide a novel arginine deiminase. Another object is to provide a method of manufacturing this novel arginine deiminase from mycoplasma. Further, the other object of the present invention is to provide an anti-cancer agent containing arginine deiminase as an effective ingredient.

The present inventors conducted research on many new types of arginine deiminase derivable from Pseudomonas, Streptococcus, mycoplasma and other microorganisms. As a result, the present invention was accomplished when it was found that a cell extract of mycoplasma contains arginine deiminase, which has its optimum pH in the physiological range, shows a high stability, and consequently provides strong inhibiting activities against the growth of cancer cells.

Arginine deiminase (EC 3.5.3.6.) is an enzyme that hydrolyzes amidino group of L-arginine into L-citrulline and ammonia, and is called by a general name of arginine dihydrolase, arginine desiminase, or guanidinodesiminase. The resultant L-citrulline is decomposed into ornithine and carbamoyl phosphate, and this carbamoyl phosphate is further decomposed into ammonia and water. ATP is produced in this process. In other words, arginine deiminase is an enzyme involved in the first step of the pathway leading to the production of ATP in connection with the metabolism of the amidino groups of arginine in bacteria and yeasts.

The arginine deiminase of the present invention has the following physicochemical properties:
(a) Function
   Hydrolyzes the amidino groups of L-arginine into L-citrulline and ammonia.
(b) Optimum pH: 6.0–7.5
(c) Stable pH: 4.5–9.0
(d) Optimum temperature: Approx. 50° C.
(e) Km value: Approx. 0.2 mM
(f) Isoelectric point (PI): Approx. 4.7
(g) Molecular weight: Approx. 45,000
   (by SDS-polyacrylamide gel electrophoresis method)
   Approx. 90,000
   (by gel filtration HPLC method)
(h) Amino acid sequence from N-terminal
   Ser-Val-Phe-Asp-Ser-Lys-Phe-Lys-Gly-Ile-His-Val-Tyr-Ser-Glu- Also, the arginine deiminase of the present invention comprises the amino acid sequence shown in FIG. 4.

The arginine deiminase of the present invention is prepared from mycoplasma by the following method:

Any mycoplasma having an ability to produce the arginine deiminase of the present invention can be used. These types of mycoplasma include *M. arginini, M. hominis, M. salivarium, M. gallinarum* and *M. orale*. The most suitable strain is the *M. arginini* [IFO Catalog No. 14476, ATCC Catalog No. 23838 or NCTC Catalog No. 10129) available from the Institute of Fermentation, Osaka, ATCC or NCTC.

In the present invention, the above mycoplasma is cultured in a liquid medium added with arginine, at a temperature of about 37° C. for one to several days in a standing condition. This mycoplasma is a facultative anaerobic bacterium and can be grown under an anaerobic condition or in the presence of oxygen. A PPLO meat broth or the like is used, and arginine is added to the medium at a ratio of 1–10 g to 1 liter of medium.

After culturing, the cells are collected, then are suspended in a buffer solution, for example, such as a phosphate buffer solution, and are disrupted by such means as sonication; finally, the precipitates are removed through centrifugal separation or a similar method. The supernatant solution is thus obtained as a cell extraction, which undergoes a process of purification by chromatography such as gel filtration chromatography, ion-exchange chromatography, affinity chromatography and the like. As a result, an arginine deiminase having the above-mentioned physicochemical properties is obtained.

The arginine deiminase of the present invention is clearly different from the known types of arginine deiminase reported in various literature, as shown in Table 1.

TABLE 1

| Reference | (Present invention) | J.B.C. 252, 2615–2620 (1979) | J.B.C. 241, 2228–2236 (1966) | J.B.C. 250, 4580–4583 (1975) | Archives of Biochemistry and Biophysics 69, 168–197 (1957) |
|---|---|---|---|---|---|
| Source | M. arginini | M. arthritidis | M. hominis | Pseudomonas putida | Streptofaecalis |
| Molecular weight | 45,000 (SDS-PAGE) 90,000 (gel filtration HPLC) | 49,000 (SDS-PAGE) | 78,300 | 54,000 (SDS-PAGE) | not known |
| Isoelectric point | 4.7 | 7.0 | not known | 6.13 | not known |
| km | 0.2 mM | 4 µM | 0.1–0.4 mM | 0.2 mM | 0.15 mM |
| Vmax | 50 µ/mg | 18 µ/mg | 53 µmg | 58.8 µ/mg | 41 µ/mg |
| Optimum pH | 6.7–7.5 | not known | 6.5–6.7 | 6.0 | 6.8 |
| Amino acid at N-terminal | Ser | Ala | not known | not known | not known |

Further, the homology search was done between the N-amino acid sequence of the arginine deiminase of the present invention and registered proteins in the computer database, but it was found that no protein has an amino acid sequence similar to that obtained by the present invention. For these reasons, it has been concluded that the arginine deiminase of the present invention is a novel arginine deiminase.

In addition, an attempt was made in the present invention to clone the gene of arginine deiminase of *M. arginini* from the genome DNA of *M. arginini*. By DNA sequence analysis of the cloned gene, a nucleotide sequence coding for the arginine deiminase was determined, as illustrated in FIG. 4. Accordingly, the arginine deiminase of the present invention was found to contain the 409 amino acids and have a molecular weight of 46375, nearly identical with the molecular weight of proteins obtained by the SDS-polyacrylamide gel electrophoresis.

As indicated by Experiments 1 through 6, the arginine deiminase of the present invention shows a superb effect of prolonging the lives of mice carrying such cancer cells as leukemia cells, fibro-sarcoma cells and colon carcinoma cells and the like. For this reason, it is evident that the arginine deiminase of the present invention is effective in the treatment of a variety of tumors, specially malignant tumors, in humans.

The activity of arginine deiminase can be determined by causing it to produce citrulline using the method reported by Fenske et. al. [J. Bacteriol. 126, 501–510 (1976)], and by measuring the amount of the yields using the method given by Archibald [J. Biol. Chem. 156, 121–142 (1944)].

Specifically, 20 µl of arginine deiminase solution is added to 1.0 ml of 10 mM arginine [dissolved in 0.1M phosphate buffer of pH 7.0], then an enzyme reaction is allowed to take place at 37° C. for 10 minutes, and the reaction is terminated by adding 1 ml of mixed acid solution ($H_2SO_4$:$H_3PO_4$=1:3). Then, the resultant reactive solution is added with 25 µl of 3% aqueous diacetylmonooxim solution, heated at 100° C. for 20 minutes under a light-shielded condition, left to cool under a room temperature for 30 minutes, and then the amount of the citrulline yield is measured quantitatively by measuring the absorbence at 490 nm. The activity of arginine deiminase producing 1 µmol of citrulline in one minute is defined as 1 unit.

With regard to an acute toxicity of arginine deiminase, there was no case of mouse deaths due to the administration of not more than 1 mg/mouse of arginine deiminase orally or intravenously in the tail. Further, the dissection of the administered animals showed no irregularities in their organs, thus affirming the high safety of arginine deiminase.

BRIEF DESCRIPTION OF THE DRAWINGS

FIGS. 4a–4c show the complete amino acid sequence of the arginine deiminase, and the nucleotide sequence which codes for the enzyme. FIG. 5 through FIG. 8 show the nucleotide sequence and amino acid sequence thereto of the oligonucleotide used as probes.

DETAILED DESCRIPTION OF PREFERRED EMBODIMENTS

Examples of the present invention are shown below.

EXAMPLE 1

Preparation of arginine Deiminase
(1) Culturing of *M. arginini*

A strain of *M. arginini* (IFO Catalog No. 14476) obtained from the Institute of Fermentation, Osaka was inoculated into a liquid medium [composed of 21 g of PPLO broth w/o CV (Difco), 10 g of L-arginine, 200 ml of horse serum, 100 ml of 25% freshly prepared yeast extract, 5 ml of 0.4% phenol red solution and 700 ml of distilled water, and adjusted pH to 7.0], and then cultured in a 5% $CO_2$ incubator at 37° C. for 2 days in a standing condition.
(2) Separation and purification of arginine deiminase
(A) Preparation of *M. arginini* cell extract 2 g of *M. arginini* cells were separated by centrifuging 2 liters of the liquid medium obtained according to the above (1) step, at a 7,000 rpm for 20 minutes. These *M. arginini* cells were suspended in 30 ml of 10 mM phosphate buffer of pH 7.0. The cells contained in this suspension were then disrupted by sonication, and the insoluble matter is removed by centrifugal separation. Finally, the resultant supernatant was obtained as a M. arginini cell extract.

(B) The purification of arginine deiminase

Arginine deiminase was purified from the M. arginini cell extract obtained in the above (A) step, by applying the following three different types of chromatography.

i) Gel filtration chromatography

The above M. arginini cell extract was applied to gel filtration chromatography under the following condition, using a Cellulofine GCL-2000 m [Chisso Corporation]:

| | |
|---|---|
| Column size: | 2.6 × 90 cm |
| Volume of gel: | 480 ml |
| Flow rate: | 24 ml/hr |
| Volume of fraction: | 6 ml each |
| Eluent: | 10 mM potassium phosphate buffer (pH 7.0), + 0.5 M sodium chloride |

Figure 1:
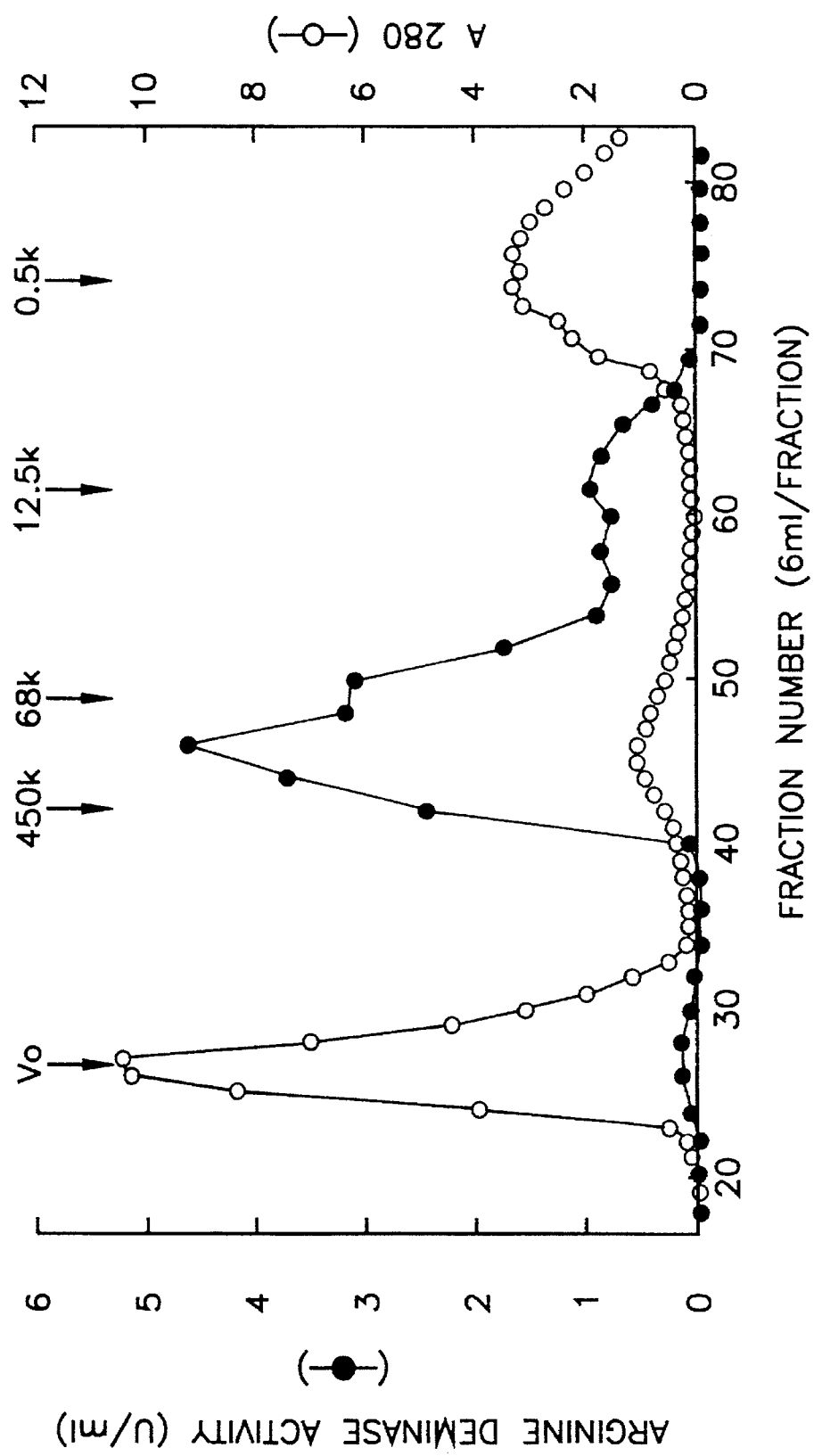
FIG. 1 shows a gel filtration chromatogram of the *M. arginini* cell extract of the present invention, FIG. 2 an ion-exchange chromatogram of the fractions 42–52 thereof, and FIG. 3 affinity chromatogram of the fractions 50–53 thereof.

The absorbance at 280 mm and arginine deiminase activity of each fraction thus obtained were measured by the aforementioned methods, and the results were as shown in FIG. 1. It was found that the arginine deiminase was contained in the fractions 42–52.

ii) Ion-exchange chromatography

The fractions 42–52 obtained in the above i) step were dialyzed for 24 hours against a 10 mM phosphate buffer. Then, the inner dialyzed solution was applied to ion-exchange chromatography under the following condition, using a DEAE-Toyopearl [Toso Co.]:

| | |
|---|---|
| Column size: | 2.6 × 30 cm |
| Volume of gel: | 320 ml |
| Flow rate: | 60 ml/hr |
| Volume of fraction: | 10 ml each |
| Eluent: | 10 mM phosphate buffer (pH 7.0) (linear gradient of sodium chloride from 0 to 0.5M) |

In other words, the dialyzed fractions containing the arginine deiminase were added into a DEAE-Toyopearl column equilibrated with the same buffer as that used in the dialysis in order to absorb arginine deiminase, and 10 ml of each fraction was collected by elution under the condition of a linear gradient of the sodium chloride concentration from 0M to 0.5M in the buffer at a flow rate of 60 ml/hr.

Figure 2:
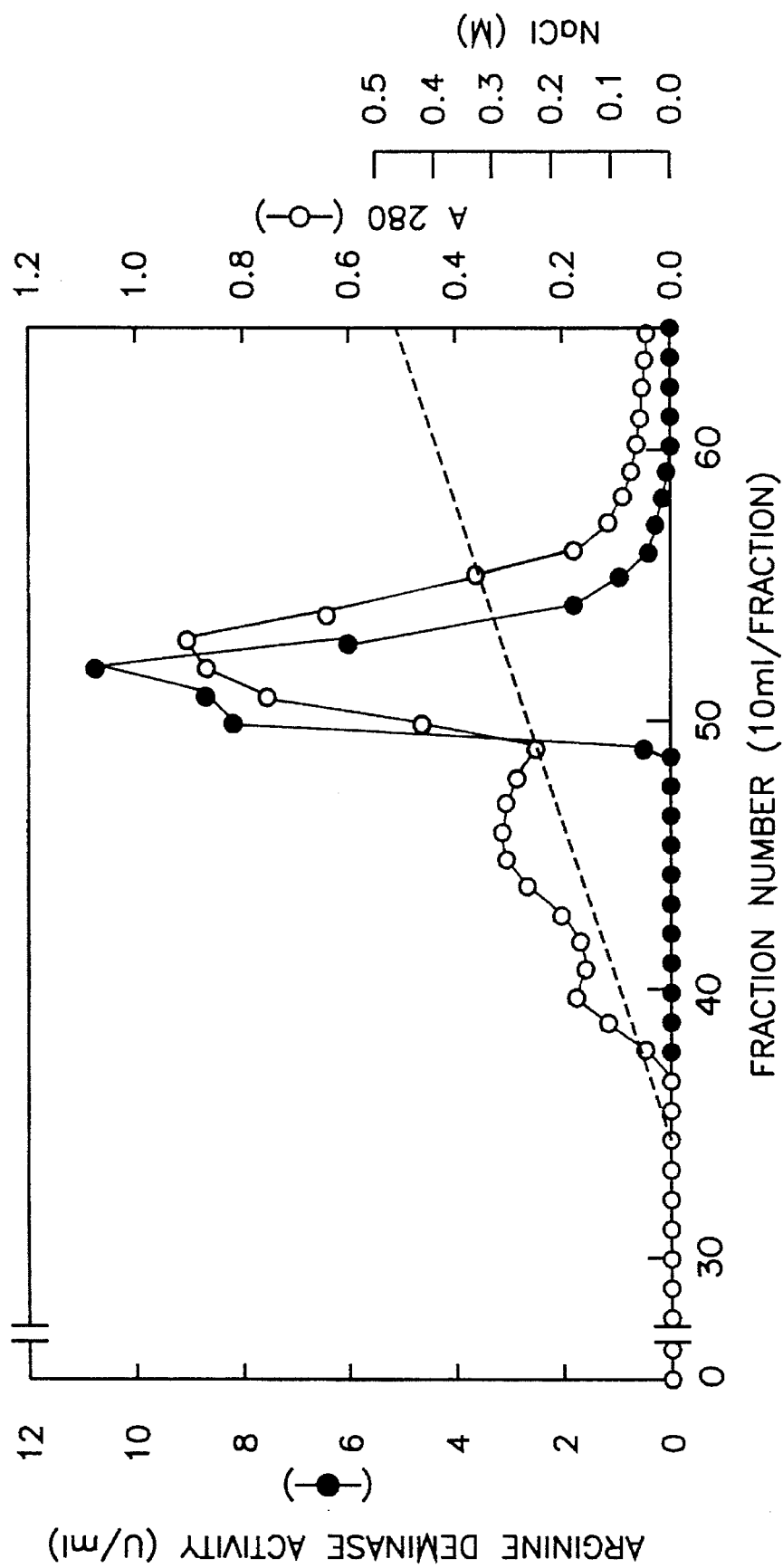

As in the above i) step, the absorbance at 280 nm and arginine deiminase activity of each fraction were measured, and the results were as shown in FIG. 2. It was found that the arginine deiminase was contained in the fractions 50–53.

iii) Affinity chromatography

The fractions 50–53 obtained in the above ii) step were dialyzed for 24 hours against a 10 mM potassium phosphate buffer. Then, the dialyzed solution was applied to affinity chromatography under the following condition, using a Arginine-Sepharose 4B [Pharmacia Co.]:

| | |
|---|---|
| Column size: | 2.2 × 10 cm |
| Volume of gel: | 38 ml |
| Flow rate: | 50 ml/hr |
| Volume of fraction: | 8 ml each |
| Eluent: | 10 mM phosphate buffer (pH 7.0) (linear, gradient of sodium chloride from 0 to |

| | |
|---|---|
| | -continued |
| | 1.0M) |

In other words, the dialyzed fractions containing the arginine deiminase were added into a Arginine-Sepharose column equilibrated with the same buffer as that used in dialysis in order to absorb arginine deiminase, and 8 ml of each fraction was collected by elution under the condition of a linear gradient from 0M to 1.0M of the sodium chloride concentration in the buffer at a flow rate of 50 ml/hr.

Figure 3:
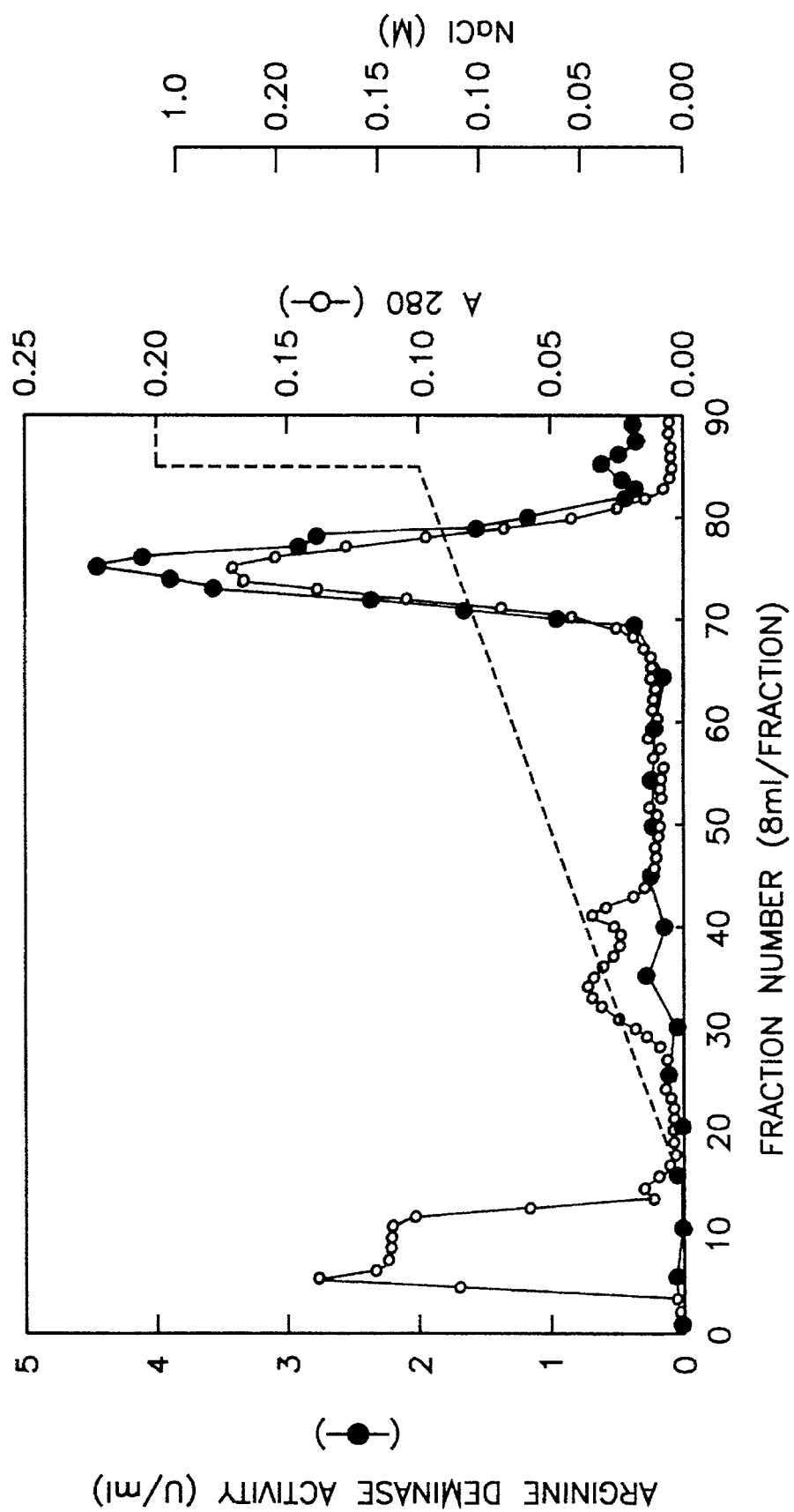

As in the above ii) step, the absorbance at 280 nm and arginine deiminase activity of each fraction were measured, and the results were as shown in FIG. 3. It was found that the arginine deiminase was contained in the fractions 71–81.

iv) SDS-polyacrylamide gel electrophoresis

The fractions 71–81 obtained in the above iii) step were analyzed by SDS-polyacrylamide gel electrophoresis according to the method reported by Laemmli et. al. [Nature, 727, 680–685 (1970)]. The purification of arginine deiminase was confirmed, as a single band was observed at a molecular weight of 45,000.

(C) Physicochemical properties of arginine deiminase

The following measurements were made with the enzyme solution obtained in the above (B) iii) step:

i) Optimum pH, optimum temperature, stable pH and stable temperature

The optimum pH range is 6.0–7.5, and the stable pH range when treated at 4° C. for 24 hours is 4.5–9.0. The highest activity is obtained in the 45°–55° C. temperature range, and as for stability against temperature, the activity is completely lost for treatment at 95° C. for 5 minutes or at 60° C. for 30 minutes.

ii) Substrate specificity

The arginine deiminase hydrolyzes L-arginine to produce L-citrulline and ammonia.

iii) Molecular weight

Measurement by the SDS-polyacrylamide gel electrophoresis indicated a molecular weight of approximately 45,000.

Measurement by the gel filtration HPLC method using a TSK G3000SW$_{XL}$ [Toso Co.] indicated a molecular weight of approximately 90,000.

iv) Isoelectric point

Measurement of the isoelectric point by the electrofocusing method indicated an isoelectric point of approximately 4.7.

v) Km value and Vmax value

By the Lineweaver-Burk plot analysis Km and Vmax were determined as 0.2 mM and 50 U/mg, respectively.

vi) The amino acid sequence from the N-terminal was determined by a peptide sequencer [Applied Biosystem Co.] as follows:

Ser-Val-Phe-Asp-Ser-Lys-Phe-Lys-Gly-Ile-His-Val-Tyr-Ser-Gluvii) Biological Activity The arginine deiminase showed an inhibiting activity against the growth of cancer cells in vitro, and indicated a superb effect of prolonging the lives of cancer-carrying mice in vivo.

EXAMPLE 2

(1) Preparation of mycoplasma genome DNA

M. arginini [IFO Catalog No. 14476] was lysed by SDS, and then was treated first by protinase K and then by RNase A. Then, the solution was extracted with phenol and then with chloroform; finally, genome DNA was prepared by dialyzing the resultant aqueous layer against 10 mM tris-hydrochloric acid (pH 8.0) in 1 mM EDTA.

(2) Preparation of mycoplasma genes library

The mycoplasma genome DNA prepared in the above (1) step was digested by appropriate restriction enzymes, then was inserted to a plasmidvector pUC19 [Toyobo Co.]; finally, this vector was introduced into *E. coli* HB101 [purchased as competent cells from Takara Shuzo Co.], to provide a mycoplasma genes library.

(3) Design and synthesis of oligonucleotide for hybridization probe

It was previously reported that the DNA of mycoplasma contains only a small amount of GC [Proc. Natl. Acad. Sci., 84, 166–169 (1987)]. In view of this finding, an oligonucleotide having 24 bases (a mixture of 4 types, and see FIG. 5 through 8 for their sequences) was designed from the N-terminal amino acid sequence of the arginine deiminase, and was synthesized by a DNA synthesizer [ABI model 308 B].

(4) Screening by colony hybridization

The oligonucleotide synthesized in the above (3) step was labeled by 32p, and was used as a probe for screening the mycoplasma gene library produced in the (2) step. Thus, positive clones were isolated.

(5) Determination of nucleotide sequences

Plasmid DNA was prepared from the clones obtained in the above (4) step, and the DNA fragment to be hybridized with the probe was integrated into M13mp19 [Toyobo Co.]. Using the dideoxy method, the nucleotide sequence was determined for both strands of the cloned gene. The results are shown in FIG. 4.

A 1230 bp open reading frame including a nucleotide sequence coding for the N-terminal, 30 amino acids sequence of the arginine deiminase was found in the cloned gene, and the 1227 bp genes, following the initiation codon ATG, were identified as the arginine deiminase gene of *M. arginini* (see FIG. 4). Since it is known that the TGA codon is recognized as a tryptophan codon in mycoplasma [Proc. Natl. Acad. Sci., 82, 2306–2309 (1985)], the TGA codons existing at 5 different positions in the arginine deiminase genes were considered as tryptophan codons, and the analysis was performed on the assumption that there were only 2 termination codons, TAA and TAG.

The molecular weight derived from the total 409 amino acids was 46375, which is nearly identical with the molecular weight obtained by the protein SDS-polyacrylamide gel electrophoresis.

EXAMPLE 3

Preparation of formulated arginine deiminase

The fractions 71–81 obtained in the Example 1 (2) iii) step were dialyzed for 24 hours against a phosphate buffered saline (PBS) (pH 7.4), and the dialyzed product was diluted by PBS in a 0.2–2.0 mg/ml solution. Then, the solution was sterilized by filtration with a 0.2 μm filter, to prepare an aqueous solution-type arginine deiminase preparation.

EXAMPLE 4

Expression of Arginine Deiminase by Transformant (1) Production of Mutant Gene

In accordance with the Kunkel method [Proc. Natl. Acad. Sci. USA, 82, 488 (1985)], point mutation was carried out to replace all of the 5 TGA codons of the arginine deiminase gene (shown in FIG. 4) by TGG codons which are the tryptophan codons of *E. coli*, using 5 different types of oligonucleotide as primers. Then, clones in which all of the 5 TGA codons have been replaced by TGG codons were selected by the plaque hybridization method using the above oligonucleotide as a probe. The selected clones were sequenced to make sure that all of the 5 TGA codons had been replaced by TGG codons.

(2) Preparation of Arginine Deiminase expressing Vector (pAD 12)

Plasmid pAD 12 was prepared by inserting, into the Sac I-Hind III site of plasmid pVC 19, genes containing the structural genes and regulatory genes 240 bq upstream therefrom of the mutant arginine deiminase genes obtained in the above (1) step. The resultant plasmid pAD 12 was found to have a promoter sequence of mycoplasma arginini arginine deiminase, and an analysis of the base sequence of the pAD 12 indicated the presence of a consensus sequence (SD, $-10$, $-35$ sequence) of the procaryotic cell promoter. Thus, it was considered possible that the plasmid pAD 12 serve as a vector expressing arginine deiminase of *E. coli*.

(3) Culturing of Transformants and preparation of Cell Extract

The pAD 12 prepared in the above (2) step was introduced to *E. coli* HB 101 (Takara Shuzo Co.), and the resultant transformant was cultured overnight at 37° C. in a 5 ml LB medium [1.0% Bacto Tryptone (DIFCO Co.), 0.5% Bacto Yeast Extract (DIFCO Co.), 0.2% glucose, 1.0% NaCl, pH 7.5]. Then, 1 ml of the culture medium was added to 250 ml of LB medium to be cultured overnight at 37° C. The cell collected from the culture by centrifugation was washed twice with physiological saline, and were suspended in 2 ml of 0.1M potassium phosphate buffer (pH 7.0). Then, the cells were disruped by sonication, and the supernatant after the removal of insolubles by centrifugation was obtained as the cell extract. The same process was repeated to prepare a cell extract of *E. coli* HB 101 retaining the pUC 19 which did not contain arginine deiminase genes. This extract was used as the control.

(4) Measurement of Arginine Deiminase Activity

The HB 101 cell extract retaining pAD 12 and the HB 101 cell extract retaining pUC 19 (control) both obtained in the (3) step were diluted 10 times by a 0.1M potassium phosphate buffer (pH 7.0), and 10 μl of each resultant solution was incubated at 37° C. for 5 hours. Then, the amount of citrulline yield was measured by the aforementioned method. The amount of arginine deiminase expression in the HB 101 retaining pAD 12 was calculated from the difference between the amount of the citrulline yield in the HB 101 retaining pAD 12 and that in the HB 101 retaining pUC 19. The result indicated 1.2 unit of arginine deiminase activity for every 250 ml of LB medium.

In addition, test results concerning the anti-cancer effects of the arginine deiminase of the present invention are presented in the experiments below.

Experiment: Anti-cancer effects of arginine deiminase

Experiment 1

Method Using Cultured Strains of Human Cancer Cells

First, $1 \times 10^4$ cells of each type of human cancer cells were inoculated in a 24-well microplate containing 1.0 ml of DME medium with a 10% serum of bovine fetal serum, and the arginine deiminase preparation obtained in the above step was added to this medium, in such an amount that the concentration of this preparation in the medium was 5 ng/ml or 10 ng/ml. Then, after culturing in a 5% $CO_2$ incubator at 37° C. for 3 days, the number of cancer cells were counted using an automated cell counter (Coultor counter) [Coultor Co.]. As the control, the same amount of PBS was added to the medium instead of the arginine deiminase preparation. The inhibiting activity against cancer cell growth was indicated in terms of the number of cancer cells in samples, relative to the corresponding number for the control which was set as 100. The results are as shown in Table 2.

TABLE 2

| Type of cell | No. of cells (% of control) | |
|---|---|---|
| | 5 ng/ml | 10 ng/ml |
| Human liver cancer cell (HLE) | 16.7 | 6.7 |
| Human malignant fibro-sarcoma cell (B32) | 20.1 | 10.3 |
| Human squamous carcinoma cancer cell (Caski) | 31.6 | 22.9 |
| Human squamous carcinoma cancer cell (HSC-4) | 57.4 | 41.8 |
| Human malignant melanoma cells (VMRC) | 41.7 | 23.4 |
| Human nasopharyngeal carcinoma cell (KB) | 57.1 | 46.9 |
| Human lung carcinoma cells (A549) | 42.3 | 45.8 |

Experiment 2

Method Using Mouse Leukemia Cells

A total of 21 male $CDF_1$ mice (BALB/c♀×DBA/B♂), 7 weeks old, were used, as subjects, and $1\times10^5$ cells of leukemia cells L1210 were transplanted i.p. to each mouse. Then, 9 mice were randomly selected as a control group, and the other were equally devided into 2 test groups. The aforementioned arginine deiminase preparations were chronically injected i.p. to the test groups daily for 8 days. The control group animals were administered with PBS.

Experiment 3

Method Using Mouse Fibro-sarcoma Meth A

A total of 27 male $CDF_1$ mice (BALB/c♀×DBA/2♂), 7 weeks old, were used as subjects, and $1\times10^6$ cells of fibro-sarcoma cells Meth A were transplanted i.p. to each mouse. Then, 9 mice were randomly selected as a control group, and the others were equally devided into 2 test groups. The arginine deiminase preparations were chronically injected i.p. to the test groups daily for 10 days. The control group animals were administered with PBS.

Experiment 4

Method Using Mouse Colon carcinoma Cells Colon 26

A total of 25 male $CDF_1$ mice (BALB/c♀×DBA/2♂), 7 weeks old, were used as subjects, and $1\times10^6$ cells of colon carcinoma cells Colon 26 were transplanted i.p. to each mouse. Then, 9 mice were randomly selected as a control group, and the others were equally devided into 2 test groups. The arginine deiminase preparations were chronically injected i.p. to the test groups daily for 14 days. The control group animals were administered with PBS.

Experiment 5

Method Using Mouse Sarcoma 180

A total of 24 male ICR mice, 7 weeks old, were used as subjects, and $1\times10^6$ cells of Sarcoma 180 cells were transplanted i.p. to each mouse. Then, 8 mice were randomly selected as a control group, and the others were equally devided into 2 test groups. The arginine deiminase preparations were chronically injected i.p. daily for 14 days to the test groups. The control group animals were administered with PBS.

Experiment 6

Method Using Mouse Ascites Hepatoma MH 134

A total of 26 male C3H/HeN mice, 7 weeks old, were used as subjects, and $1\times10^6$ cells of Ascites Hepatoma MH 134 were transplanted i.p. to each mouse. Then, 10 mice were randomly selected as a control group, and the others were equally devided into 2 groups. The arginine deiminase preparations were chronically injected i.p. daily for 14 days to the test groups. The control group animals were administered with PBS.

The anti-cancer effect was indicated in terms of the percentage (T/C %) of the average number of days lived by the test groups in comparison with that by the control group. The results obtained from the above Experiments 2 through 6 are shown in Tables 3 through 7, respectively.

TABLE 3

| (L1210) | | |
|---|---|---|
| Group | Ave. No. of days lived | T/C (%) |
| Control (N = 9) | 8.4 ± 0.7 | (100) |
| 0.25 mg/mouse (N = 6) | 9.3 ± 0.5 | 111 |
| 0.5 mg/mouse (N = 6) | 10.3 ± 1.4 | 126 |

TABLE 4

| (Meth A) | | |
|---|---|---|
| Group | Ave. No. of days lived | T/C (%) |
| Control (N = 9) | 10.6 ± 1.6 | (100) |
| 0.1 mg/mouse (N = 9) | 10.7 ± 0.7 | 101 |
| 0.5 mg/mouse (N = 9) | 12.6 ± 1.7 | 118 |

TABLE 5

| (Colon 26) | | |
|---|---|---|
| Group | Ave. No. of days lived | T/C (%) |
| Control (N = 9) | 11.1 ± 1.3 | (100) |
| 0.1 mg/mouse (N = 8) | 11.9 ± 1.4 | 107 |
| 0.5 mg/mouse (N = 8) | 21.8 ± 4.6 | 196 |

TABLE 6

| (Sarcoma 180) | | |
|---|---|---|
| Group | Ave. No. of days lived | T/C (%) |
| Control (N = 8) | 21.3 ± 9.9 | (100) |
| 0.04 mg/mouse (N = 8) | 35.3 ± 13.3 | 166 |
| 0.2 mg/mouse (N = 8) | 48.4 ± 9.0 | 228 |

TABLE 7

| | (MH 134) | |
|---|---|---|
| Group | Ave. No. of days lived | T/C (%) |
| Control (N = 10) | 25.0 ± 6.7 | 100 |
| 0.04 mg/mouse (N = 8) | >75 | >300 |
| 0.2 mg/mouse (N = 8) | >75 | >300 |

We claim

1. A purified arginine deiminase which hydrolyzes the amidino group of L-arginine into L-citrulline and ammonia, and having a molecular weight of approximately 45,000, as determined by SDS-polyacrylamide gel electrophoresis, an iso-electric point of approximately 4.7, and an amino acid sequence as shown in FIGS. 4a, 4b, and 4c.

2. A purified arginine deiminase obtained from Mycoplasma arginini (IFO catalog No. 14476) and having the following physicochemical properties:

(a) Function and substrate specificity:
     Hydrolyzes the amidino groups of L-arginine into L-citrulline and ammonia
  (b) Optimum pH: 6.0–7.5
  (c) Stable pH: 4.5–9.0
  (d) Optimum temperature: Approx. 50° C.
  (e) Km value: Approx. 0.2 mM
  (f) Isoelectric point (pI): Approx. 4.7
  (g) Molecular weight: Approx. 45,000
     (by SDS-polyacrylamide gel electrophoresis)
     Approx. 90,000
     (by gel filtration HPLC method)
  (h) Amino acid sequence: an amino acid sequence as shown in FIGS. 4a, 4b and 4c.

\* \* \* \* \*

UNITED STATES PATENT AND TRADEMARK OFFICE
CERTIFICATE OF CORRECTION

PATENT NO. : 5,474,928
DATED : December 12, 1995
INVENTOR(S) : Haruo Takaku, et al.

It is certified that error appears in the above-indentified patent and that said Letters Patent is hereby corrected as shown below:

```
On the title page:

In item [75]: inventor's name "Karuo Takaku" should read --Haruo Takaku--.

In item [73]: the assignee should read --Japan

Energy Corporation, Tokyo, Japan--.
```

Signed and Sealed this

Second Day of July, 1996

Attest:

BRUCE LEHMAN

*Attesting Officer*  *Commissioner of Patents and Trademarks*